(12) United States Patent
Carver et al.

(10) Patent No.: US 7,531,357 B2
(45) Date of Patent: May 12, 2009

(54) PREPARATION OF PLATELET ANALOGS

(75) Inventors: Franklin J. Carver, Benicia, CA (US); James D. Lapicola, Alamo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 162 days.

(21) Appl. No.: 11/099,361

(22) Filed: Apr. 4, 2005

(65) Prior Publication Data

US 2006/0223187 A1 Oct. 5, 2006

(51) Int. Cl.
G01N 31/00 (2006.01)
G01N 33/48 (2006.01)

(52) U.S. Cl. ............... 436/10; 436/8; 436/17; 436/18; 436/63; 436/174; 435/2; 252/408.1

(58) Field of Classification Search ............ 436/8, 436/10, 17, 18, 63, 174; 435/2; 252/408.1
See application file for complete search history.

(56) References Cited

U.S. PATENT DOCUMENTS

| | | | |
|---|---|---|---|
| 2,656,508 A | 10/1953 | Coulter | |
| 4,160,644 A | 7/1979 | Ryan | |
| 4,179,398 A | 12/1979 | Hunt | |
| 4,198,206 A | 4/1980 | Ryan | |
| 4,219,440 A | 8/1980 | Runck et al. | |
| 4,264,470 A | 4/1981 | Chastain, Jr. et al. | |
| 4,302,355 A | 11/1981 | Turner, Jr. et al. | |
| 4,324,686 A | 4/1982 | Mundschenk | |
| 4,338,564 A | 7/1982 | Mundschenk | |
| 4,356,172 A | 10/1982 | Nakao et al. | |
| 4,389,490 A | 6/1983 | Crews et al. | |
| 4,390,632 A * | 6/1983 | Carter, II | 436/10 |
| 4,405,719 A | 9/1983 | Crews et al. | |
| 4,436,821 A | 3/1984 | Ryan | |
| 4,698,312 A | 10/1987 | Wong et al. | |
| 4,704,364 A * | 11/1987 | Carver et al. | 436/10 |
| 5,008,201 A | 4/1991 | Ryan | |
| 5,429,797 A | 7/1995 | Camiener | |
| 5,439,667 A | 8/1995 | Camiener | |
| 5,994,139 A * | 11/1999 | Jacobs et al. | 436/10 |
| 6,146,901 A | 11/2000 | Carver et al. | |
| 6,200,500 B1 * | 3/2001 | Ryan | 252/408.1 |
| 6,221,668 B1 * | 4/2001 | Ryan et al. | 436/8 |
| 6,265,148 B1 | 7/2001 | Ryan | |
| 6,331,435 B1 | 12/2001 | Hengstenberg | |
| 6,342,391 B1 | 1/2002 | Chen et al. | |
| 6,399,388 B1 * | 6/2002 | Ryan et al. | 436/8 |
| 6,403,377 B1 * | 6/2002 | Ryan et al. | 436/8 |
| 6,406,915 B2 | 6/2002 | Ryan et al. | |
| 6,509,192 B1 * | 1/2003 | Young | 436/10 |
| 6,514,763 B2 | 2/2003 | Carver et al. | |
| 6,653,063 B2 | 11/2003 | Carver et al. | |
| 6,762,055 B2 | 7/2004 | Carver et al. | |
| 6,962,817 B2 * | 11/2005 | Li et al. | 436/63 |
| 7,109,036 B2 * | 9/2006 | Ortiz et al. | 436/8 |
| 7,135,341 B2 * | 11/2006 | Ortiz et al. | 436/10 |
| 2003/0054330 A1 | 3/2003 | Fischer et al. | |
| 2003/0104631 A1 | 6/2003 | Carver et al. | |

FOREIGN PATENT DOCUMENTS

WO WO 83/02328 A1 7/1983
WO WO 01/84138 A1 11/2001

OTHER PUBLICATIONS

Wong et al.; "Preparation of platelet analogs from resealed red cell ghosts: Effect of red blood cell mean cell volume"; 2001, *Clinical Chemistry*, vol. 47, No. 6, pp. A158.
Shalev, Oded et al.; "Catalysis of Soluble Hemoglobin Oxidation by Free Iron on Sickle Red Cell Membranes"; 1996, *Blood*, vol. 87, No. 9, pp. 3948-3952.
Shinar, E. et al.; "Oxidative denaturation of red blood cells in thalassemia"; 1990, Semin Hematol., vol. 27, No. 1, 2 page abstract.
Tamai, Mazda; "A Method for Drying Red Blood Cells for Solid-Phase Immunoassay"; 1999, *Transfusion Medicine*, vol. 9, No. 4, 2 page abstract.

\* cited by examiner

*Primary Examiner*—Maureen M Wallenhorst
(74) *Attorney, Agent, or Firm*—Townsend and Townsend and Crew LLP.; M. Henry Heines

(57) ABSTRACT

Erythrocytes from a vertebrate animal other than a human that have been size reduced and treated with a fixing agent by conventional methods to resemble human platelets are further treated to achieve a size distribution that is detected in a consistent manner by different methodologies of blood cell counting. The further treatment includes heating to a denaturing temperature followed by a second treatment with a fixing agent. The resulting cells are useful as controls for calibrating and checking the accuracy of automated blood cell counting equipment.

28 Claims, 9 Drawing Sheets

PREPARATION OF PLATELET ANALOGS

BACKGROUND OF THE INVENTION

1. Field of the Invention

This invention resides in the field of reference and control materials for hematology instrumentation, with particular attention to simulated human platelets used as controls for automated platelet counting.

2. Description of the Prior Art

Automated blood cell analyzers that provide cell counts for each of the various types of cells present in a sample of blood do so by measurements of the electrical and/or optical properties of each cell type. These properties include electrical impedance, electrical conductance, radio frequency modulation, light scattering, and light absorption, in various combinations. A variety of analyzers are commercially available and used in clinical laboratories, individual analyzers differing in the manner in which they collect and process the data.

Federal regulations require that blood cell analyzers be checked regularly against controls to verify the reliability of the analyzers. The controls are synthetic suspensions that have the certain physical and chemical characteristics similar to those of blood and that include stable cells or particles whose sizes and shapes closely approximate those of the different cells present in human blood. Unfortunately, the different methodologies among the various instruments react to controls in different ways, and certain types of control particles that serve as effective substitutes for one kind of cell on a particular instrument have been found to appear like another type or even like cell debris on a different instrument.

Among the various types of cells in human blood that must be represented in a control, platelets are particularly problematic. The use of actual platelets in the control is unfavorable since platelets disintegrate when the blood in which they are suspended escapes from the vascular system, and the disintegration causes the liberation of thromboplastins that cause blood clotting. In addition, platelets are easily activated and tend to aggregate, and are expensive. For these reasons, simulated platelets have been developed that are less costly and that lack these unfavorable characteristics. Simulated platelets are typically biological cells or non-biological particles. When biological cells are used, they are cells other than platelets that have been modified to bear characteristics that render them detectable by the same parameters as actual platelets and thereby distinguishable from other cell types. When particles are used, they are particles that have these characteristics. The characteristics differ depending on the methodology of the detection. In some cases, the distinguishing characteristics are size range and size distribution, while in others, the chemical contents, such as a lack of hemoglobin as compared to the presence of hemoglobin in a red blood cell, serve as the differentiating characteristics. For a control to be useful in different types of instruments rather than only one, it is important that the simulated platelet component be detectable as platelets regardless of the methodology of the instrument. This, unfortunately, is not always the case, even when the measured characteristic is size distribution, i.e., it is not uncommon for a particular control to be read as having one size distribution by one means of detection and another by a different means of detection. Fresh human platelets have a log-normal size distribution rather than a Gaussian distribution, and detection instrumentation that relies on particle size also must have either controls that have a log-normal distribution or a computer algorithm that can accept a population that approaches a log-normal size distribution.

A relatively inexpensive substitute for actual human platelets and one that lacks the disintegration and aggregation characteristics of human platelets are red blood cells from non-human vertebrates. To render these cells useful as simulated platelets, the cells are reduced in size and treated with a fixing agent to toughen the cell membranes. Goats are a favored source of red blood cells as substitutes for platelets, since goat red blood cells can either be altered or blended to a size and size distribution similar to those of human platelets. One method of size adjustment is the suspension of the cells in a hyperosmotic solution to draw cellular fluid from the cells by osmotic pressure. The fixing treatment is performed either before or after the use of osmotic pressure, depending on whether the fixing treatment is used as a means of controlling or limiting the rate of passage of cellular fluid when osmotic pressure is applied.

When the fixing treatment is done to control the rate of fluid passage through the cell membrane, the purpose is to achieve a desired particle size range and size distribution. Achieving a particular particle size range and distribution as measured by optical techniques however does not always result in the same size range and distribution as measured by electrical techniques. One method of correcting this deficiency is disclosed by Ryan, W. L. (Streck Laboratories, Inc.), U.S. Pat. No. 5,008,201, issued Apr. 16, 2001. This method involves preparing a graduated series of particle sizes by subjecting different populations of cells to different degrees of fixation to cause each population to shrink to a different degree when osmotic pressure is applied. The populations are then combined in proportions that will collectively approximate the desired size distribution. This is labor-intensive and susceptible to error in both the selected proportions and the differing degrees of treatment.

SUMMARY OF THE INVENTION

It has now been discovered that platelet analogs with a size range and distribution detected by optical measurement that conform closely to the size range and distribution detected by electrical measurement can be prepared from red blood cells of a vertebrate animal other than a human that have already been shrunken in size and fixed. The preparation method involves first heating the size-reduced and fixed cells to a temperature above ambient temperature for a period of time sufficient to have a denaturing effect on the cells, then exposing the cells to a fixing agent, preferably before or after cooling the cells to a temperature at or close to ambient temperature. Effective results with this method can be achieved without the need for separately preparing distinct lots of cells of different sizes and combining the lots in carefully selected proportions to achieve a combination that approximates the desired size distribution. The process can instead be performed on a single lot and still achieve the desired distribution as detected by both electrical and optical modes of measurement. This preparation method brings the size and distribution characteristics closer to those that enable the shrunken cells to be used as controls for evaluating actual human platelets.

While not intending to be bound by any particular theory, the inventors herein believe that a possible reason for the improved performance is related to the creation of a size distribution that is closer to log-normal than to Gaussian, since a log-normal distribution more closely resembles that of actual human platelets. The method of the invention is also believed to modify the contents of the cells in a manner that changes the optical refractivity of the cells to a value that more closely resembles the optical refractivity of human platelets.

DETAILED DESCRIPTION OF THE INVENTION AND PREFERRED EMBODIMENTS

Figure 1:
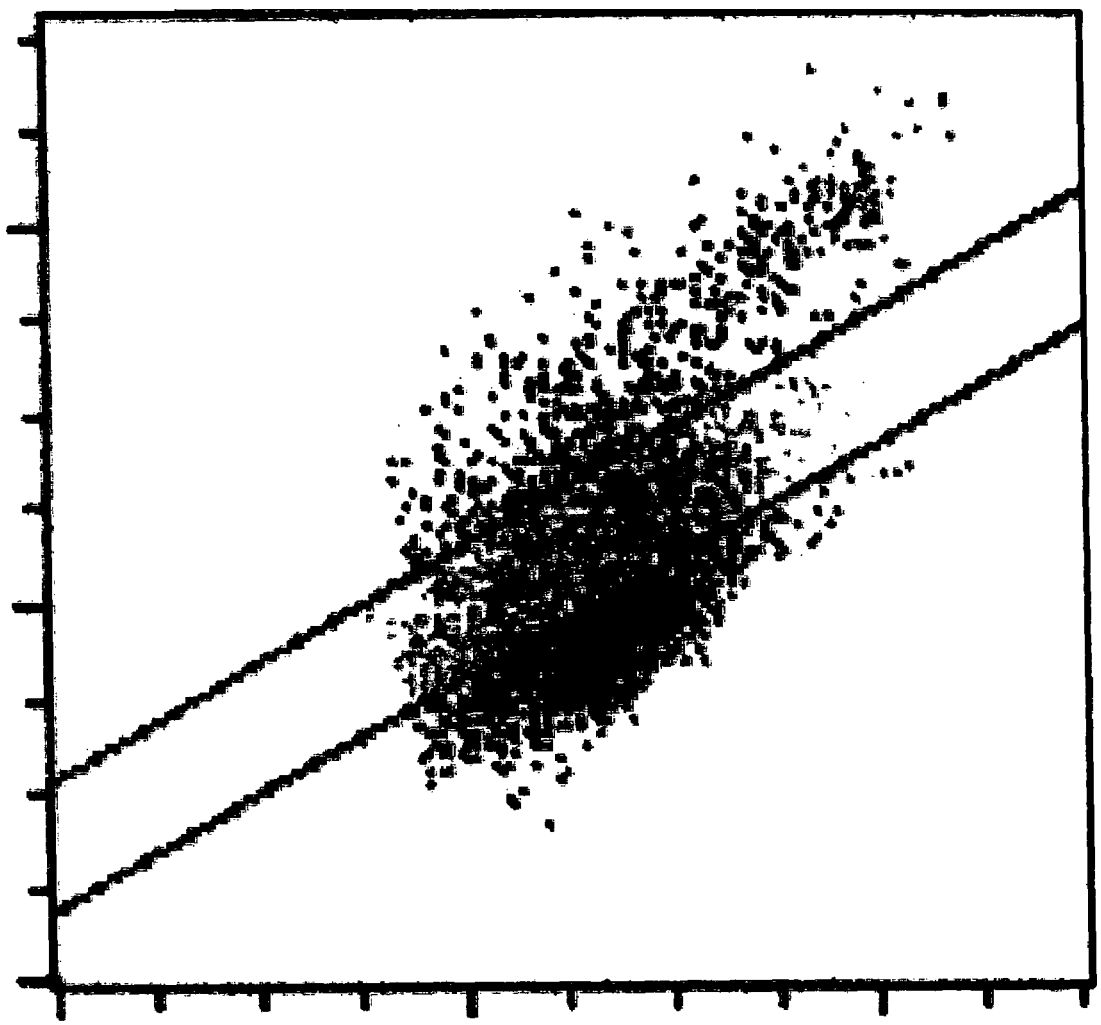
FIG. 1 is a scattergram of small-size platelet analogs that have not been prepared in accordance with the present invention.
Figure 2:
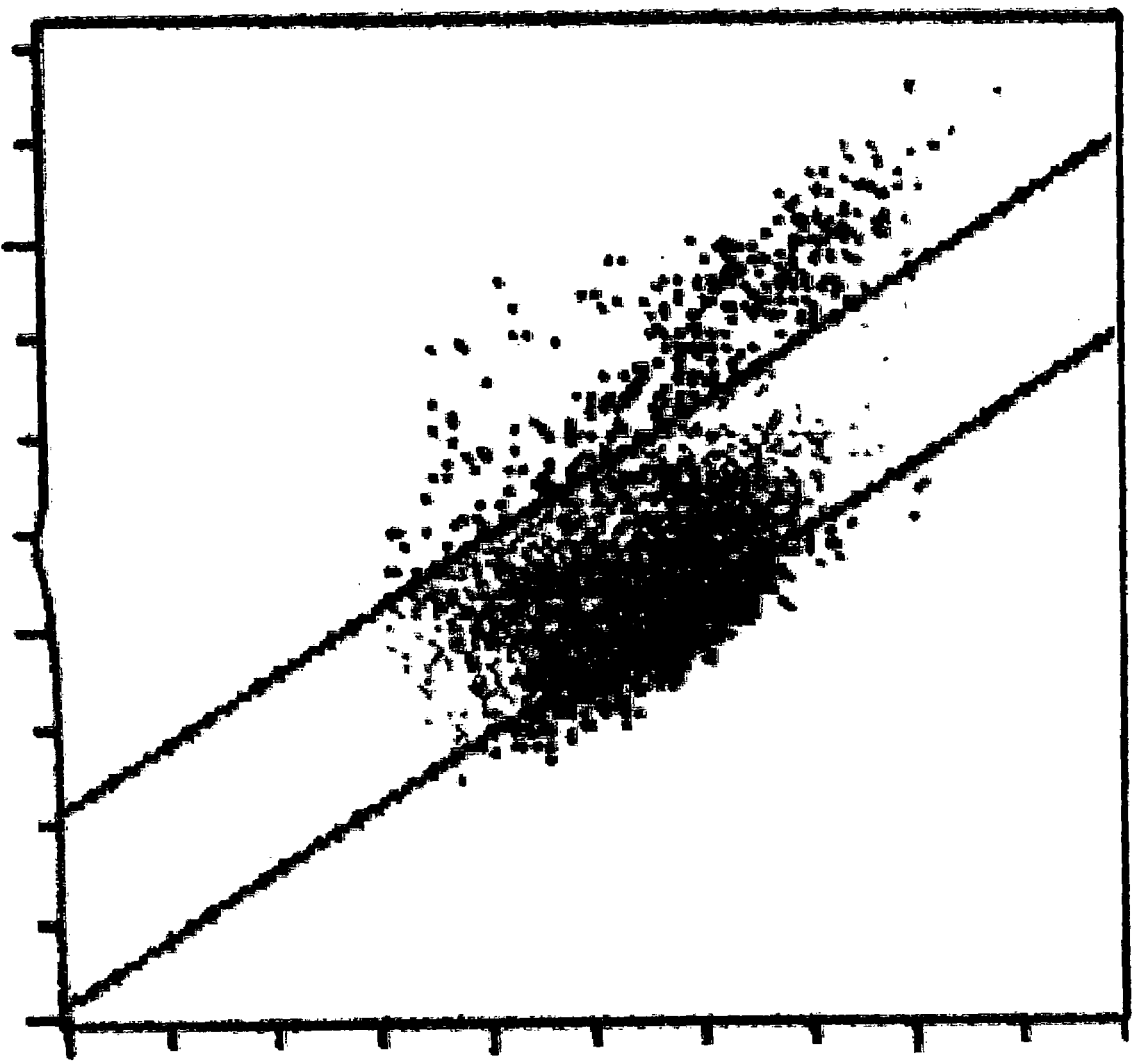
FIG. 2 is another scattergram of small-size platelet analogs that have been heated in accordance with the present invention without subsequent fixing.
Figure 3:
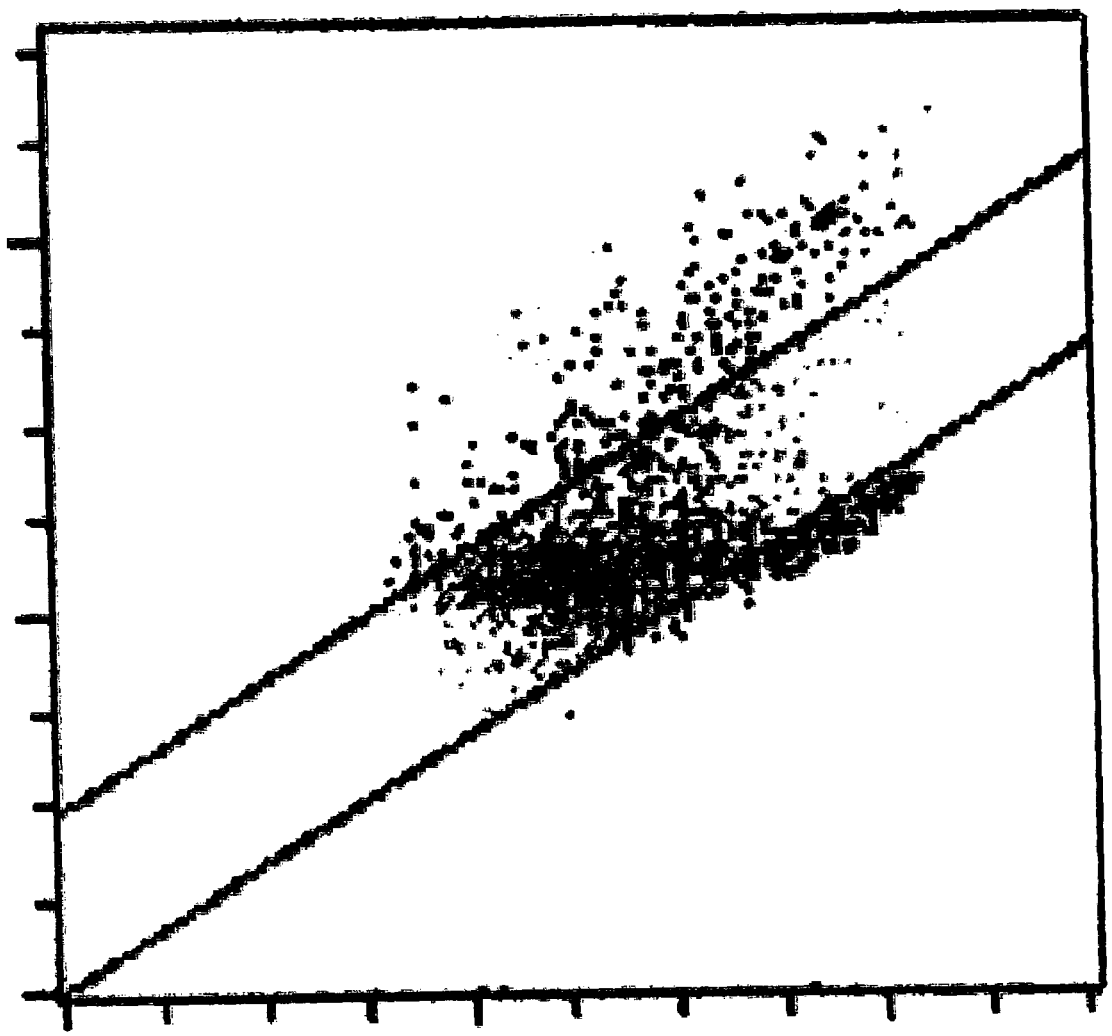
FIG. 3 is a scattergram of small-size platelet analogs that have been heated and subsequently fixed in accordance with the present invention.
Figure 4:
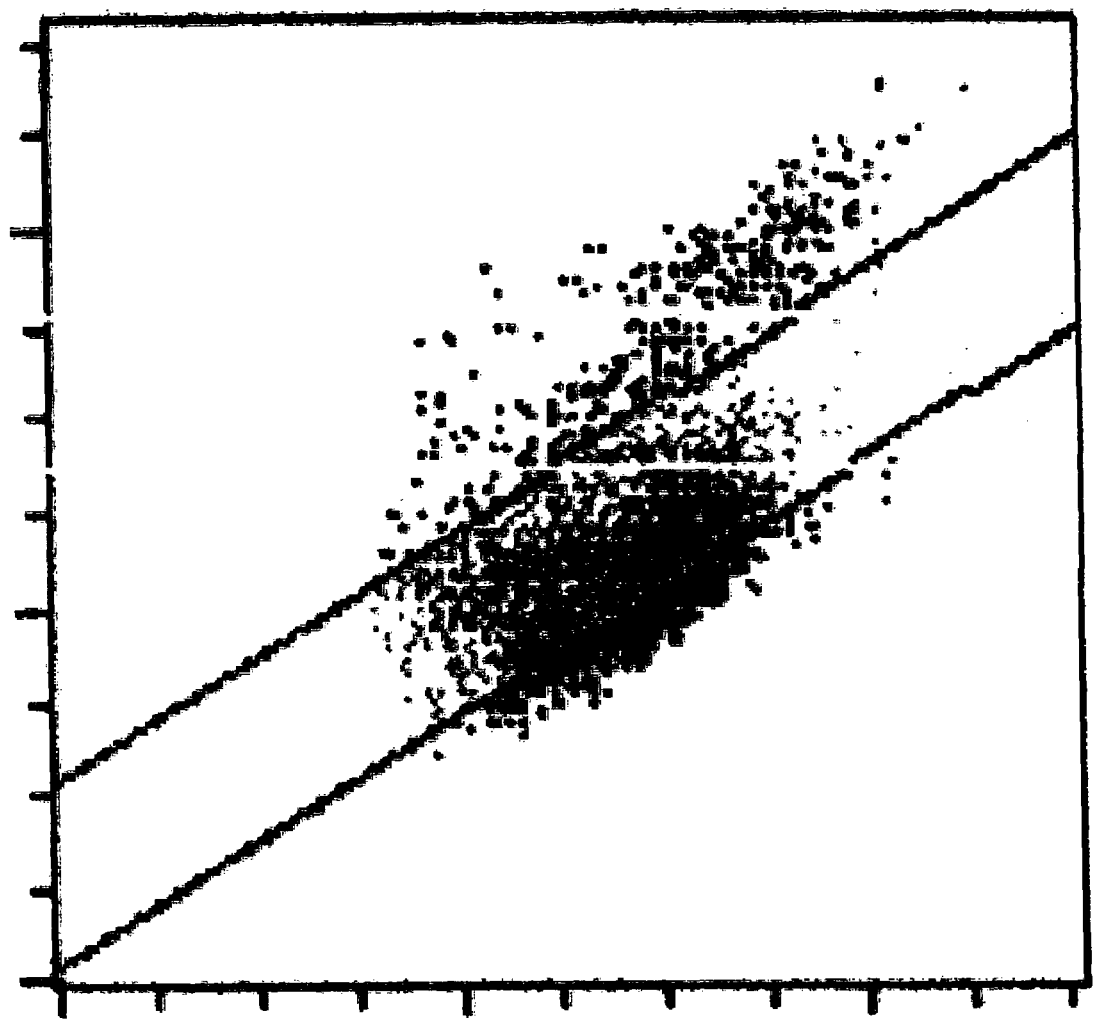
FIG. 4 is a scattergram of large-size platelet analogs that have not been prepared in accordance with the present invention.
Figure 5:
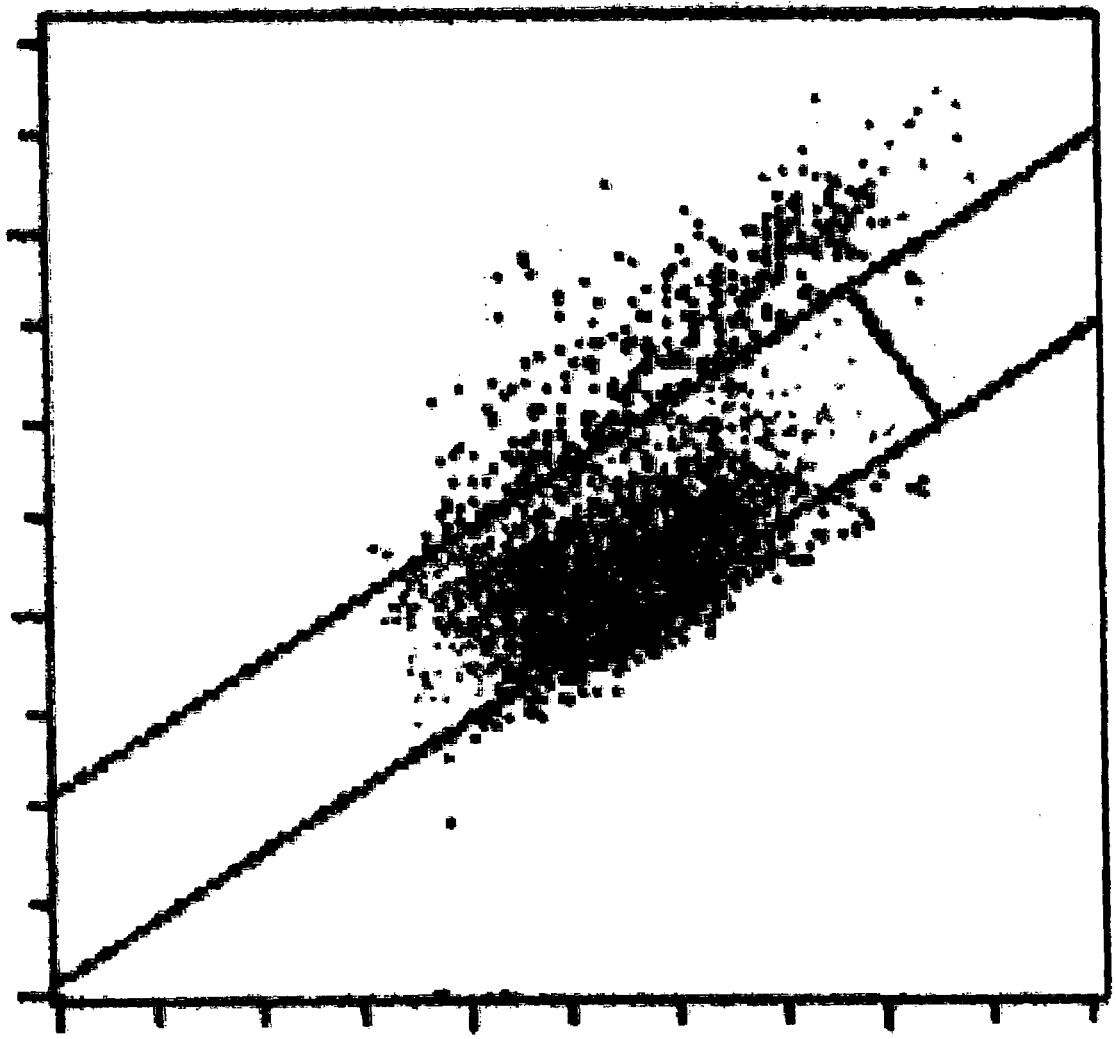
FIG. 5 is another scattergram of large-size platelet analogs that have been heated in accordance with the present invention without subsequent fixing.
Figure 6:
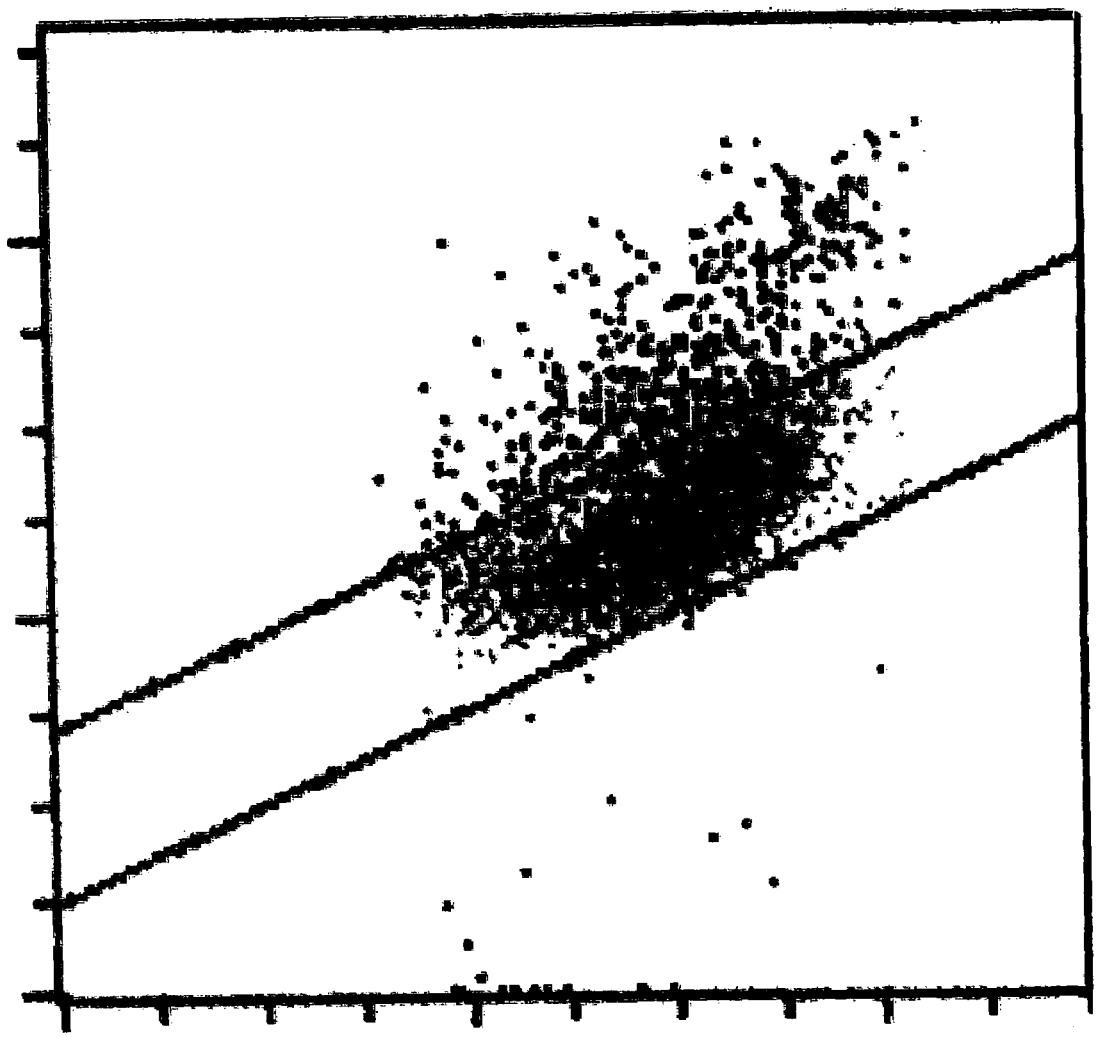
FIG. 6 is a scattergram of large-size platelet analogs that have been heated and subsequently fixed in accordance with the present invention.

While red blood cells from vertebrate animals in general other than human can be used in the practice of this invention, goat red blood cells (erythrocytes) are prominently cited in the prior art for this purpose. The volume and size distribution range of goat erythrocytes vary to some extent with the age and sex of the goat as well as hereditary factors, breeding history and the manner and environment in which the goat was raised. In general, however, goat erythrocytes have a mean erythrocyte volume that is two to three times the mean platelet volume of human platelets.

Methods of preparing goat erythrocytes to bring them into the size range of human platelets are known in the art. Included among these methods are the extraction of controlled amounts of cellular fluid from the erythrocytes by osmotic pressure as indicated above, in conjunction with fixation of the cell membrane with the use of fixing agents, likewise as indicated above. Additional treatments and treatment agents are used in some cases as well, including anticoagulants and stabilizers, for example, and the application of heat in some cases to anneal cells after the extraction of cellular fluid. All of these treatments, however combined and in whatever order, prepare the erythrocytes for the processing steps that constitute the present invention. The size range of the erythrocytes prior to processing in accordance with the invention, expressed herein by the term "mean platelet volume" despite the fact that the erythrocytes are platelet analogs rather than true platelets, can vary. In most cases, best results will be achieved with a size range of from about 7 femtoliters to about 15 femtoliters, preferably from about 9 femtoliters to about 15 femtoliters, and most preferably from about 10 femtoliters to about 13 femtoliters.

The first step in the practice of the invention is the heating of the size-reduced erythrocytes to a sufficient temperature and for a sufficient period of time to achieve a denaturing effect. This thermal treatment is of sufficient degree and duration to achieve this effect without damage to or coagulation of the cells. The temperature may vary with the length of time the cells are held at the temperature. In most cases, the most efficient results in terms of treatment time will be obtained by heating to a temperature of about 50° C. or higher, preferably from about 50° C. to about 75° C., and most preferably from about 50° C. to about 60° C. Preferred heating periods are from about 4 hours to about 48 hours, preferably in some cases from about 4 hours to about 24 hours, and preferably in some cases about 24 hours or more. While the temperature and time of heating can vary, greater heating times and higher heating temperatures will result in treated cells that are smaller in cell volume. Thus, one can control the final cell size to a certain extent by selection of the heating temperature and time. If desired, the heating can be performed in a closed container to avoid evaporation of liquid or exposure to the atmosphere. It may also be desirable, although not strictly necessary, to perform the heating in an inert or non-oxidizing atmosphere. Most effective results for the treatment as a whole are generally obtained when the heating step is performed without the inclusion of a fixing agent. Fixing agents, as discussed below, are thus preferably added after the denaturing temperature has been maintained for the designated period of time.

The treatment with a fixing agent that follows the heat treatment is performed with fixing agents already known in the art for the treatment of platelets, erythrocytes, and blood cells in general, and other methods of treatment known in the art can likewise be used. Examples of fixing agents are glutaraldehyde, formaldehyde, osmium tetroxide, mercuric chloride, acrolein, and tannic acid. These can be used singly or in combinations, and fixing agent preparations that are commercially available can be used as well. One example of a commercially available fixing agent is HistoChoice® fixative (Amresco Inc., Solon, Ohio, USA). Other examples are fixatives known as Zenker's (American Master Tech Scientific, Inc., Lodi, Calif., USA), B5, B3 (both of American Master Tech Scientific, Inc., Lodi, Calif., USA), and Bouin's (Medical Chemical Corporation, Torrance, Calif., USA). Aldehyde crosslinking fixing agents are preferred, examples of which are glutaraldehyde and formaldehyde. A particularly preferred fixing agent is glutaraldehyde.

The amount of fixative used is not critical to the invention and can vary widely. In most cases, efficient results will be achieved with approximately 3% to 30% (by volume) of a liquid reagent grade fixative relative to the suspension of the cells, where the suspension contains about 1 to about 25 parts by volume of a cell concentrate per 100 parts of suspension. Preferably, the suspension contains about 3 to about 15 parts by volume of cell concentrate per 100 parts by volume of suspension, and the fixative is added to an amount of about 5% to about 20% (by volume) relative to the suspension. Other fixation conditions are likewise not critical and may vary. The exposure time to the fixative, for example, is preferably at least about 2 hours, more preferably from about 8 hours to about 48 hours, and most preferably from about 16 to about 24 hours. Treatment with the fixative is not performed under denaturing conditions, and accordingly the treatment is generally performed at a lower temperature than the heat treatment. A temperature of less than 30° C. is preferred for the fixation step, and room (ambient) temperature is generally adequate. The atmosphere under which fixation is performed can be any atmosphere that does not chemically interfere with the fixation. Air is generally an acceptable atmosphere, although to preserve the fluid volume the suspension is preferably maintained in a sealed container during fixation.

Following denaturation and fixation, the cells can be suspended in any of a variety of fluids, including hypo-osmotic, iso-osmotic, or hyper-osmotic fluids. Iso-osmotic aqueous liquids, i.e., those that do not form an osmotic pressure differential across the membranes of the cells, are preferred since they are most compatible with the final blood control product. Conventional additives can be added for the same purposes that they serve in standard cell suspensions of the prior art. Propylene glycol, for example, can be added to clear the cytoplasm and to reduce cell-to-cell binding.

In certain embodiments of the invention, the cells are pre-conditioned prior to the heating and fixation steps of the present invention. Pre-conditioning is achieved by moderate heating for at least an hour to a temperature below the temperature ranges cited above, preferably in diluted form with an iso-osmotic diluent, a saline diluent, or water, and in some cases, with dissolved propylene glycol in any of these media. The preferred temperature range for pre-conditioning is from about 30° C. to about 40° C., and the pre-conditioning time is from about 2 hours to about 4 hours. Pre-conditioning tends to improve the agreement between the optical and electrical methods of platelet counting.

Still further improvements in the agreement between the optical and electrical methods of platelet counting are achieved by incubating the cells in a suspension of human red blood cells in addition to the various treatment steps discussed above. This incubation is preferably performed at room temperature for a period of at least one day, more preferably for at least 5 days, and most preferably for at least 10 days.

The following examples are offered only for purposes of illustration.

EXAMPLE 1

Small Batch With Small and Large Starting Particles

This example illustrates how treatment of previously prepared platelet analogs that were optimized for electrical impedance measurements can be further treated by the methods of the present invention to achieve a size, distribution, and optical refractivity that is optimal for both optical and electrical impedance particle counters. A series of platelet analogs, i.e., samples of goat erythrocytes that had already been annealed, i.e., treated by methods of the prior art to achieve size reduction by extracting cellular fluid by osmotic pressure and by fixing with a fixing agent, were suspended in a suspending medium and divided into portions. Each portion was then placed in a separate receptacle for treatment. Two lots of treated erythrocytes were used, one having a mean platelet volume (MPV) of 7.7 fL and the other a mean platelet volume of 11.5 fL. Within each size range, different samples were treated differently, in terms of the suspending medium in which the cells were placed and the subsequent treatment steps, which included the application of heat and the treatment with a fixing agent.

The general procedure was as follows. Concentrated platelet analogs, 5 mL in volume for each size, were placed in 100 mL graduated cylinders, the small-size analogs in one cylinder and the large-size in a second cylinder. Each cylinder was then filled to 100 mL with an aqueous iso-osmotic liquid. Forty-five (45) milliliters were then taken from each of the two graduated cylinders and placed in separate 50-mL centrifuge tubes. An additional 5 mL of the iso-osmotic liquid was added to each tube to bring the total volume in each tube to 50 mL.

The two tubes were placed in a water bath at 56° C. overnight. The contents of each tube were then divided in half, resulting in four tubes each containing 25 mL of incubated cell suspension. Reagent glutaraldehyde (2.5 mL) was combined with 25 mL of heated sample, mixed, and fixed at room temperature overnight. After fixation, the fixed cells were washed three times with the iso-osmotic suspending agent and then resuspended in the same suspending agent but with polyethylene glycol added. Aliquots of the cells were then centrifuged at 3,000 rpm for twenty minutes. After centrifuging, the supernatant was replaced with a suspension of human red blood cells in a physiological saline solution. Three sets of experiments were performed on each of the two analog sizes—one set without the heat treatment and without the glutaraldehyde treatment, a second set with the heat treatment only (no glutaraldehyde treatment), and a third set with both the heat treatment and the glutaraldehyde treatment.

Assays were performed on an Abbott CELL-DYN 4000 Hematology Analyzer (Abbott Laboratories, Abbott Park, Ill., USA). This Hematology Analyzer evaluates platelet-sized particles by optical and impedance methods. The assay results are shown in the scattergrams of FIGS. 1 through 6, as follows:

TABLE I

Legend for FIGS. 1-6

| FIG. | Cell Size (MPV) Before Treatment | Treatment |
|---|---|---|
| 1 | 7.7 fL | None |
| 2 | 7.7 fL | Heat Only |
| 3 | 7.7 fL | Heat and Glutaraldehyde |
| 4 | 11.5 fL | None |
| 5 | 11.5 fL | Heat Only |
| 6 | 11.5 fL | Heat and Glutaraldehyde |

In each of these scattergrams, the two parallel lines represent the limits of the optical count, the points outside of the two parallel lines representing particles that are not included in the optical count. The scattergrams with the least number of points residing outside the parallel lines are FIGS. 3 and 6, and these are therefore the samples with the best agreement between the optical count and the impedance count. These are the samples that have received both the heat treatment and the glutaraldehyde treatment.

EXAMPLE 2

Large Batch With Intermediate Size Starting Particles

The procedure of Example 1 was followed with the following exceptions. The MPV of the annealed goat red blood cells that were used as a starting material was 10.4 fL. Fifty (50) mL of the annealed red blood cell concentrate was diluted by the iso-osmotic solution to a final volume of 1 liter. The sample was then placed in a 1-L centrifuge bottle and heated in a water bath at 56° C. After heating for 24 hours, the sample was poured into a 1-L bottle containing sufficient reagent glutaraldehyde that the final solution contained 10% glutaraldehyde by volume. Fixing in glutaraldehyde was allowed to continue for 24 hours, after which time the sample was washed four times in an organic buffered saline solution.

Parallel samples prepared in the same manner were then conditioned in media containing red blood cells at room temperature for 11 days. Additional parallel sets of samples were also prepared in the same manner except that one set received neither the heating treatment nor the glutaraldehyde fixation and another set received the heating treatment only.

Assays were performed on the Abbott CELL-DYNE 4000 of Example 1. The count data from the analyzer are shown in Table II for all six samples (i.e., three having been conditioned in the red blood cell suspension and three without having been conditioned in this manner) and in FIGS. 7, 8, and 9 for the three samples that were conditioned with the red blood cell suspension. Table II lists the number of samples for each set (n) and the mean and coefficient of variance (C.V.) for each sample set.

TABLE II

Comparative Particle Count Data

| Analog Particle Size and Treatment | n | Optical Count | | Impedance Count | |
|---|---|---|---|---|---|
| | | Mean | Mean | Mean | C.V. |
| 10.4 fL<br>No Treatment, No RBCs | 1 | 6 | — | 198 | — |
| 10.4 fL<br>No Treatment, With RBCs | 7 | 103 | 52.2% | 197 | 2.8% |
| 10.1 fL<br>Heat Only, No RBCs | 1 | 15 | — | 241 | — |
| 10.1 fL<br>Heat Only, With RBCs | 6 | 95 | 77.6% | 240 | 1.3% |
| 8.3 fL<br>Heat and Glutaraldehyde, No RBCs | 1 | 245 | — | 463 | — |
| 8.3 fL<br>Heat and Glutaraldehyde, With RBCs | 20 | 204 | 2.0% | 234 | 2.1% |

Figure 7:
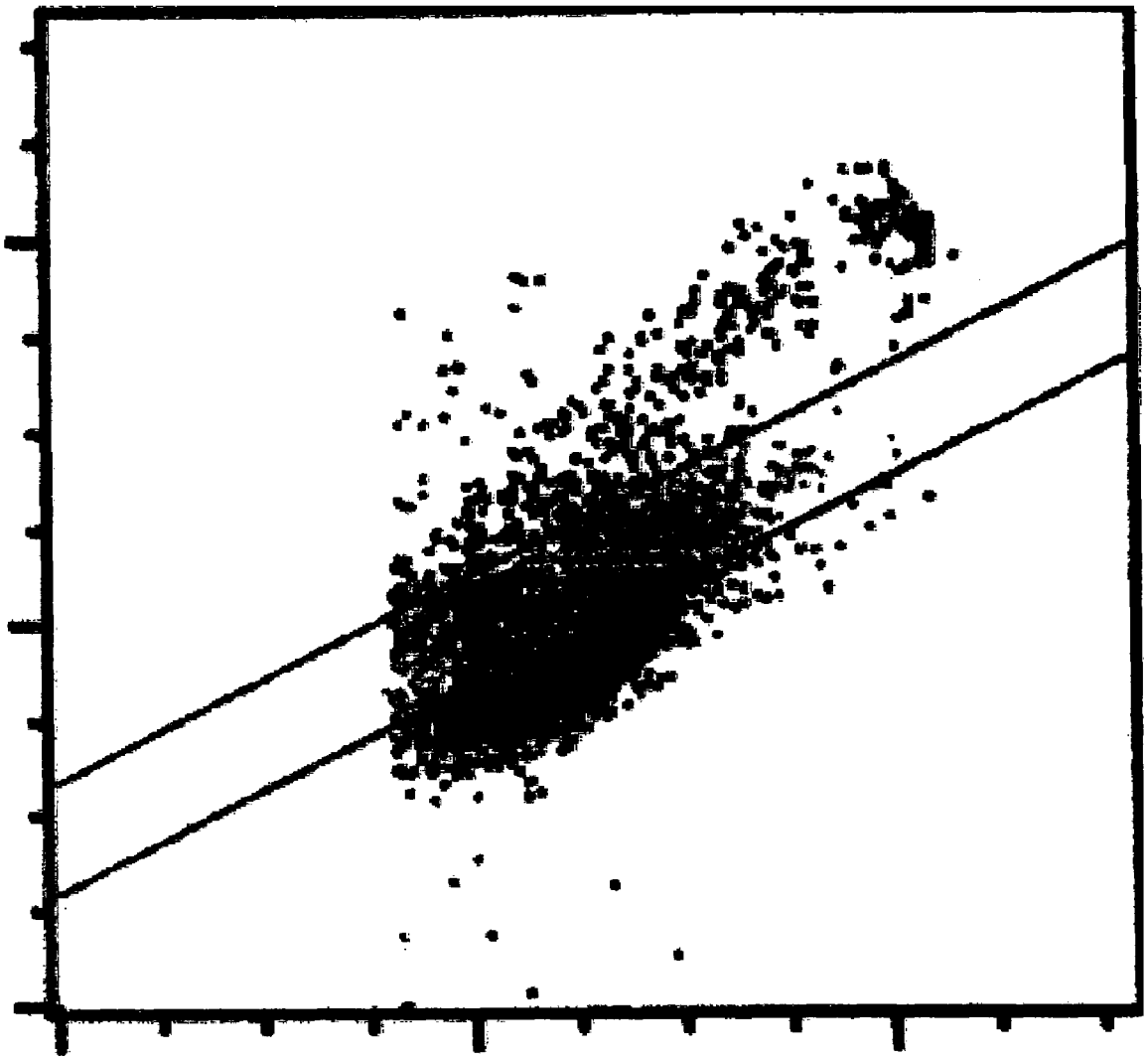
FIG. 7 is a scattergram of intermediate-size platelet analogs that have not been prepared in accordance with the present invention.
Figure 8:
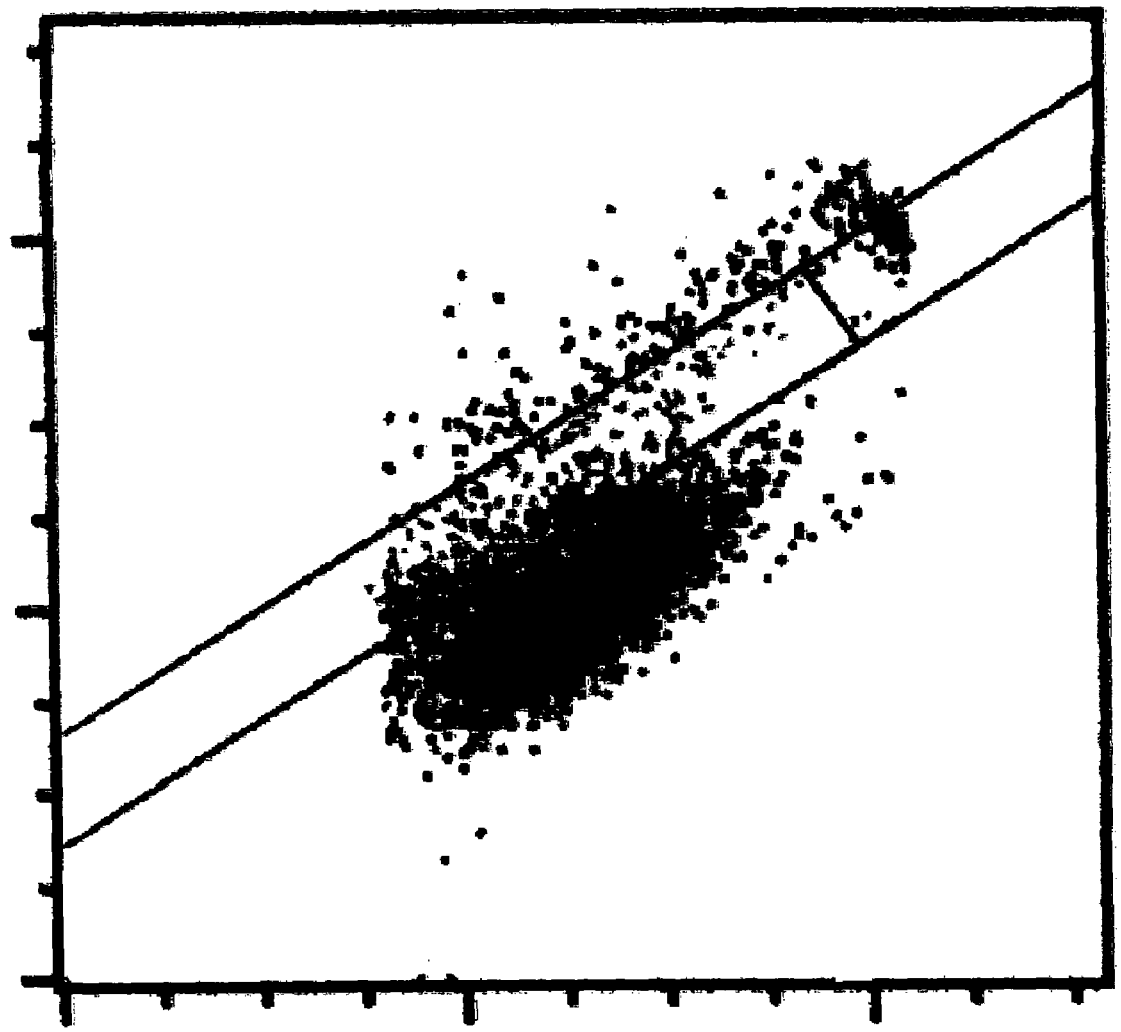
FIG. 8 is another scattergram of intermediate-size platelet analogs that have been heated in accordance with the present invention without subsequent fixing
Figure 9:
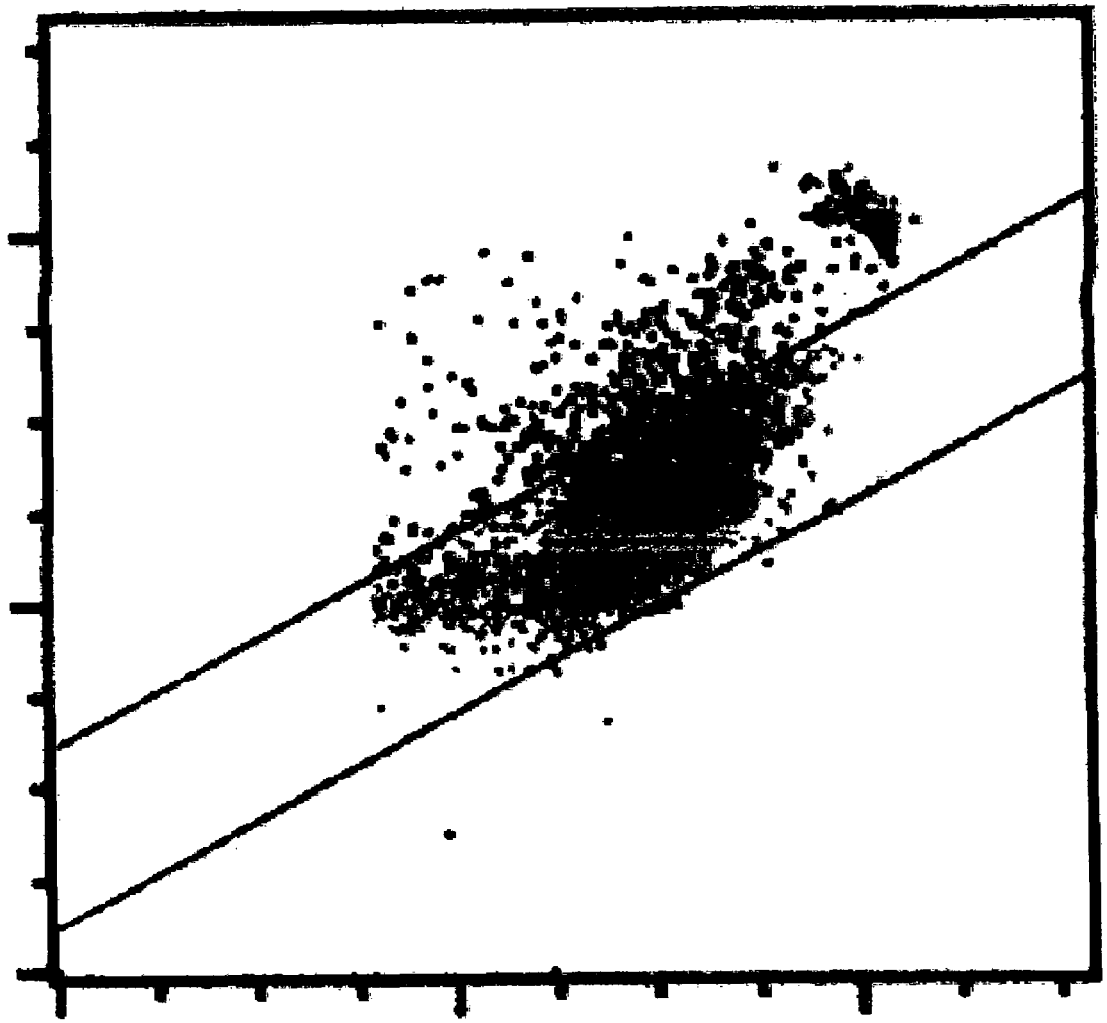
FIG. 9 is a scattergram of intermediate-size platelet analogs that have been heated and subsequently fixed in accordance with the present invention.

The data in Table II and in FIGS. 7, 8, and 9 show that the best agreement between optical count data and the impedance count data was obtained when the samples were both heated and fixed. Samples treated in this manner have the smallest proportion of points outside the parallel lines and the smallest C.V. values in both measurement methods.

EXAMPLE 3

Effects of Pre-Conditioning

This example illustrates the effects of pre-conditioning the annealed goat red blood cells prior to the heat treatment and fixation steps of the present invention. The pre-conditioning consisted of setting at room temperature or moderate heating at 37° C. for 2-4 hours in various diluents.

The diluents were the aqueous iso-osmotic solution used in the preceding examples, Ringer's saline solution, and water, used separately on individual samples. Further samples were pre-conditioned with the same diluents but further containing 20% or 40% propylene glycol by weight. Still further samples were also conditioned, subsequent to the heat and fixation treatments, in media containing human red blood cells. Following the pre-conditioning, the various samples were treated with heat and glutaraldehyde as in the preceding examples.

The results were variations in the final particle size and an improvement in platelet fit. The largest final particle sizes were observed in samples that had been preconditioned with water, and in general the final particle sizes were inversely related to the conductivity of the pre-conditioning medium. The performance, in terms of the correspondence between the optical-based and electrical impedance-based platelet counts, of samples that were pre-conditioned in media that contained less than 40% propylene glycol in any of these pre-conditioning diluents were improved by the post-conditioning.

The foregoing is offered for purposes of illustration. Further variations, modifications, and substitutions that fall within the scope of the invention will be readily apparent to those skilled in the art.

What is claimed is:

1. A process for the manufacture of human platelet analogs for use as reference controls in automated blood cell analyzers, said process comprising:
  (a) treating a single lot of red blood cells of a vertebrate other than a human that have been reduced in size by extraction of cellular fluid and fixed with a fixing agent, by heating said cells in the absence of a fixing agent for about 4 hours to about 48 hours to a sufficient degree to achieve a denaturing effect, and
  (b) reacting said single lot of cells with a fixing agent after said heating, to cause said single lot to display by optical measurement a log normal size distribution simulating that of human platelets.

2. The process of claim 1 wherein said red blood cells are goat red blood cells.

3. The process of claim 1 wherein said heating of step (a) is performed at about 50° C. to about 75° C. and from about 4 hours to about 24 hours.

4. The process of claim 1 wherein said heating of step (a) is performed at about 50° C. to about 60° C.

5. The process of claim 1 wherein step (b) is performed at a temperature below 30° C. for at least about 2 hours.

6. The process of claim 1 wherein (b) is performed at ambient temperature for 8 to 48 hours.

7. The process of claim 1 wherein (b) is performed at ambient temperature for 16 to 24 hours.

8. The process of claim 1 wherein said fixing agent of step (a) is a crosslinking fixing agent.

9. The process of claim 1 wherein said fixing agent of step (a) is a member selected from the group consisting of glutaraldehyde, formaldehyde, osmium tetroxide, acrolein, and tannic acid.

10. The process of claim 1 wherein said fixing agent of step (a) is a member selected from the group consisting of glutaraldehyde and formaldehyde.

11. The process of claim 1 wherein said fixing agent of step (a) is glutaraldehyde.

12. The process of claim 1 wherein said red blood cells of step (a) prior to heating have a mean platelet volume of from about 7 to about 15 femtoliters.

13. The process of claim 1 wherein said red blood cells of step (a) prior to heating have a mean platelet volume of from about 9 to about 15 femtoliters.

14. The process of claim 1 wherein said red blood cells of step (a) prior to heating have a mean platelet volume of from about 10 to about 13 femtoliters.

15. Modified blood cells for use as analogs of human platelets in reference controls for automated blood cell analyzers, prepared by a process comprising:
  (a) treating a single lot of red blood cells of a vertebrate other than a human that have been reduced in size by extraction of cellular fluid and fixed with a fixing agent, by heating said cells to a denaturing temperature in the absence of a fixing agent for about 4 hours to about 48 hours to achieve a denaturing effect, and
  (b) reacting said cells with a fixing agent after said heating, to cause said single lot of red blood cells to display by optical measurement a log normal size distribution simulating that of human platelets.

16. The modified blood cells of claim 15 wherein said red blood cells are goat red blood cells.

17. The modified blood cells of claim 15 wherein said denaturing temperature is from about 50° C. to about 75° C. and said heating is performed for a period of from about 4 hours to about 24 hours.

18. The modified blood cells of claim 15 wherein said denaturing temperature is from about 50° C. to about 60° C.

19. The modified blood cells of claim 15 wherein step (b) is performed at a temperature below 30° C. for at least about 2 hours.

20. The modified blood cells of claim 15 wherein step (b) is performed at ambient temperature for 8 to 48 hours.

21. The modified blood cells of claim 15 wherein step (b) is performed at ambient temperature for 16 to 24 hours.

22. The modified blood cells of claim 15 wherein said fixing agent of step (a) is a crosslinking fixing agent.

23. The modified blood cells of claim 15 wherein said fixing agent of step (a) is a member selected from the group consisting of glutaraldehyde, formaldehyde, osmium tetroxide, and tannic acid.

24. The modified blood cells of claim 15 wherein said fixing agent of step (a) is a member selected from the group consisting of glutaraldehyde and formaldehyde.

25. The modified blood cells of claim 15 wherein said fixing agent of step (a) is glutaraldehyde.

26. The modified blood cells of claim 15 wherein said red blood cells of step (a) prior to heating have a mean platelet volume of from about 7 to about 15 femtoliters.

27. The modified blood cells of claim 15 wherein said red blood cells of step (a) prior to heating have a mean platelet volume of from about 9 to about 15 femtoliters.

28. The modified blood cells of claim 15 wherein said red blood cells of step (a) prior to heating have a mean platelet volume of from about 10 to about 13 femtoliters.

* * * * *